(12) United States Patent
Osborn, III et al.

(10) Patent No.: US 6,171,292 B1
(45) Date of Patent: *__Jan. 9, 2001__

(54) TOILET-DISPOSABLE ABSORBENT INTERLABIAL DEVICE

(75) Inventors: Thomas Ward Osborn, III, Cincinnati; Bradley Neil Johnson, West Chester, both of OH (US)

(73) Assignee: The Procter & Gamble Company, Cincinnati, OH (US)

( * ) Notice: Under 35 U.S.C. 154(b), the term of this patent shall be extended for 0 days.

This patent is subject to a terminal disclaimer.

(21) Appl. No.: 09/473,462

(22) Filed: Dec. 28, 1999

Related U.S. Application Data (63) Continuation of application No. 09/082,667, filed on May 21, 1998, now Pat. No. 6,033,391, which is a continuation of application No. 08/883,606, filed on Jun. 26, 1997, now Pat. No. 5,762,644, which is a continuation-in-part of application No. 08/876,206, filed on Jun. 16, 1997, and a continuation-in-part of application No. 08/869,897, filed on Jun. 5, 1997, and a continuation-in-part of application No. 08/778,520, filed on Jan. 3, 1997, now Pat. No. 5,895,381, and a continuation-in-part of application No. 08/778,925, filed on Jan. 3, 1997, now abandoned, and a continuation-in-part of application No. 08/778,521, filed on Jan. 3, 1997, and a continuation-in-part of application No. 08/706,371, filed on Aug. 30, 1996, now Pat. No. 5,885,265.

(51) Int. Cl.$^7$ ...................................................... A61F 13/15

(52) U.S. Cl. .......................................................... 604/385.17
(58) Field of Search ................................... 604/904, 363, 604/385.01, 385.17, 385.18

(56) References Cited

U.S. PATENT DOCUMENTS 5,762,644 * 6/1998 Osborn, III et al. ........... 604/385.17
6,033,391 * 3/2000 Osborn, III et al. ........... 604/385.17

* cited by examiner

*Primary Examiner*—Dennis Ruhl
(74) *Attorney, Agent, or Firm*—Matthew P. Fitzpatrick (57) ABSTRACT

Absorbent devices, and more particularly toilet-disposable absorbent devices that are worn interlabially by female wearers for catamenial purposes, incontinence protection, or both, are disclosed. The absorbent interlabial device of the present invention comprises a central absorbent portion and preferably a pair of flexible extensions joined to the central absorbent portion. The main absorbent portion comprises an upper portion, and a lower portion opposed to the upper portion. In use, the upper portion is positioned furthest inward into the space between the wearer's labia majora. The pair of flexible extensions extends downwardly and laterally outward from the upper portion of the main absorbent portion, and preferably is capable of maintaining contact with the inside surfaces of the wearer's labia majora when the wearer's body goes through a range of motions, including squatting. Additionally, the flexible extensions are preferably capable of covering the fingertips of the wearer as the absorbent device is inserted into the interlabial space. The components of the absorbent device are preferably biodegradable. The device disperses into a plurality of fragments when exposed to mildly agitated room temperature water. The small size of the device contributes to its flushability. The dispersibility, flushability, and biodegradability of the device all contribute to the ability of the device to be effectively and reliably disposed of in a toilet.

2 Claims, 5 Drawing Sheets

TOILET-DISPOSABLE ABSORBENT INTERLABIAL DEVICE

CROSS REFERENCE TO RELATED APPLICATIONS

This application is a continuation of application Ser. No. 09/082,667, filed May 21, 1998 now U.S. Pat. No. 6,033,391, which is a continuation of application Ser. No. 08/883,606, filed Jun. 26, 1997, now U.S. Pat. No. 5,762,644, which is a continuation in part of: application Ser. No. 08/876,206, filed on Jun. 16, 1997, pending; application Ser. No. 08/869,897, filed on Jun. 5, 1997, pending; application Ser. No. 08/778,520, filed on Jan. 3,1997, now U.S. Pat. No. 5,895,381; application Ser. No. 08/778,925, filed on Jan. 3, 1997, now abandoned; application Ser. No. 08/778,521, filed on Jan. 3, 1997, pending; and application Ser. No. 08/706,371, filed on Aug. 30, 1996, now U.S. Pat. No. 5,885,265.

FIELD OF THE INVENTION

This invention relates to absorbent devices, and more particularly to a toilet-disposable absorbent device having flexible extensions that is worn interlabially by female wearers for catamenial purposes, incontinence protection, or both.

BACKGROUND OF THE INVENTION

All manner and variety of absorbent articles configured for the absorption of body fluids such as menses, urine and feces are, of course, well known. With respect to feminine protection devices, the art has offered two basic types; sanitary napkins have been developed for external wear about the pudendal region while tampons have been developed for internal wear within the vaginal cavity for interruption of menstrual flow therefrom. Such tampon devices are disclosed in U.S. Pat. No. 4,412,833, entitled "Tampon Applicator", issued to Weigner, et al. on Nov. 1, 1983, and U.S. Pat. No. 4,413,986, entitled "Tampon Assembly With Means For Sterile Insertion", issued to Jacobs on Nov. 8, 1983.

Hybrid devices which attempt to merge the structural features of the sanitary napkins and the tampons into a single device have also been proposed. Such hybrid devices are disclosed in U.S. Pat. No. 2,092,346, entitled "Catamenial Pad", issued to Arone on Sep. 7, 1937, and U.S. Pat. No. 3,905,372, entitled "Feminine Hygiene Protective Shield", issued to Denkinger on Sep. 16, 1975. Other less intrusive hybrid devices are known as labial or interlabial sanitary napkins and are characterized by having a portion which at least partially resides within the wearer's vestibule and a portion which at least partially resides external of the wearer's vestibule. Such devices are disclosed in U.S. Pat. No. 2,662,527, entitled "Sanitary Pad", issued to Jacks on Dec. 15, 1953, and U.S. Pat. No. 4,631,062, entitled "Labial Sanitary Pad", issued to Lassen, et al. on Dec. 23, 1986.

Interlabial pads have the potential to provide even greater freedom from inconvenience because of their small size and increased wearer discretion. Numerous attempts have been made in the past to produce an interlabial pad which would combine the best features of tampons and sanitary napkins while avoiding at least some of the disadvantages associated with each of these types of devices. Examples of such devices are described in U.S. Pat. No. 2,917,049 issued to Delaney on Dec. 15, 1959, U.S. Pat. No. 3,420,235 issued to Harmon on Jan. 7, 1969, U.S. Pat. No. 4,595,392 issued to Johnson, et al. on Jun. 17, 1986, and U.S. Pat. No. 5,484,429 issued to Vukos, et al. on Jan. 16, 1996. A commercially available interlabial device is the FRESH 'N FIT® Padette which is marketed by Athena Medical Corp. of Portland, Oreg. and is described in U.S. Pat. Nos. 3,983,873 and 4,175,561 issued to Hirschman on Oct. 5, 1976 and Nov. 27, 1979, respectively.

Many of these devices have not met with great commercial success, however. There are drawbacks associated with all of the above products. For example, the device described in the Delaney patent does not appear to be capable of an easy and comfortable insertion, due to the possibility of the layers of absorbent material opening up during insertion. The commercially available Padettes suffer from the disadvantage that they may not consistently cover the vaginal introitus and/or the urethra during all body motions (e.g., when the wearer is squatting). The Padette product also may not reliably be expelled as intended when wearer urinates.

Interlabial devices should preferably be designed to be dispelled by a stream of urine which dislodges the product so that it falls into a conventional toilet where it can be flushed. It is important that any such product quickly disintegrate into the sewer system so that it does not obstruct or otherwise damage the sewage systems. It is also important, however, that the product maintain sufficient integrity while it is worn so that it does not disintegrate or tear in use.

Thus, a need exists for an interlabial device that is small in size and that can be easily inserted and that provides protection against incontinence, menstrual discharges, and discharges of bodily exudates throughout a great range of wearer motions. A need also exists for an interlabial device that will reliably be expelled when the wearer urinates. A need also exists for an interlabial device which facilitates sanitary insertion and removal. That is, a need exists for a device which may be inserted into the interlabial space of a wearer while covering the fingertips, thus preventing the fingertips from becoming soiled. A need also exists for an absorbent interlabial device which will maintain its integrity when worn so that it does not disintegrate or tear in use. A need further exists for an interlabial device which is disposable in a conventional toilet thereby facilitating a convenient disposal when the device is expelled by urination, or optionally, removed with the fingers.

SUMMARY OF THE INVENTION

This invention relates to absorbent devices, and more particularly to a toilet-disposable absorbent device that is insertable into the interlabial space of a female wearer for catamenial purposes, incontinence protection, or both.

The absorbent interlabial device of the present invention comprises a central portion and a pair of flexible extensions joined to the central absorbent portion. The central absorbent portion comprises an upper portion and a lower portion opposed to the lower portion. The upper portion faces toward the vestibule floor of the wearer during insertion of the absorbent device into the wearer's interlabial space and during use. That is, the upper portion is positioned furthest inward into the space between the wearer's labia thus leading the lower portion of the absorbent device during insertion. Upon insertion, the lower portion is less fully inserted into the wearer's interlabial space than the upper portion and the lower portion faces away from the floor of the vestibule of the wearer.

The flexible extensions extend downwardly and outwardly from the upper portion of the central absorbent portion and are joined to the same. Preferably, the flexible extensions are capable of maintaining contact with inside surfaces of the wearer's labia and covering a substantial portion of the same. The flexible extensions are also preferably capable of covering the wearer's fingertips as the absorbent device is inserted into the interlabial space of the wearer.

Preferably, the absorbent interlabial device is at least partially constructed from biodegradable materials.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

DETAILED DESCRIPTION OF THE INVENTION

Figure 1:
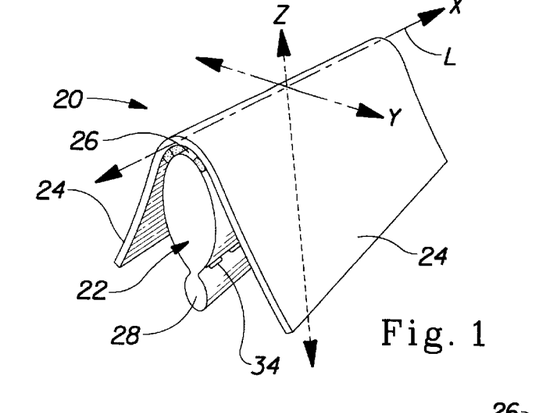
FIG. 1 is a perspective view of a preferred embodiment of the absorbent interlabial device of the present invention.

The present invention is directed to a toilet-disposable absorbent interlabial device. FIG. 1 shows one preferred embodiment of the absorbent interlabial device of the present invention, interlabial device 20. The present invention, however, can be in many other forms, and is not limited to a structure having the particular configuration shown in the drawings.

As used herein the term "absorbent interlabial device" refers to a structure which has at least some absorbent components, and is specifically configured to reside at least partially within the interlabial space of a female wearer during use. Preferably, more than half of the entire absorbent interlabial device 20 of the present invention resides within such interlabial space, more preferably substantially the entire absorbent interlabial device 20 resides within such interlabial space, and most preferably the entire absorbent interlabial device 20 resides within such interlabial space of a female wearer during use.

As used herein, the term "interlabial space" refers to that space in the pudendal region of the female anatomy which is located between the inside surfaces of the labia majora extending into the vestibule. Located within this interlabial space are the labia minor, the vestibule and the principal urogenital members including the clitoris, the orifice of the urethra, and the orifice of the vagina. Standard medical authorities teach that the vestibule refers to the space bounded laterally by the inside surfaces of the labia minora and extending interiorly to the floor between the clitoris and the orifice of the vagina. Therefore, it will be recognized that the interlabial space as defined above may refer to the space between the inside surfaces of the labia majora, including the space between the inside surfaces of the labia minora also known as the vestibule. The interlabial space for purposes of the present description does not extend substantially beyond the orifice of the vagina into the vaginal interior.

The term "labia" as used herein refers generally to both the labia majora and labia minora. The labia terminate anteriorly and posteriorly at the anterior commissure and the posterior commissure, respectively. It will be recognized by those skilled in the art that there is a wide range of variation among women with respect to the relative size and shape of labia majora and labia minora. For purposes of the present description, however, such differences need not be specifically addressed. It will be recognized that the disposition of the absorbent interlabial device into the interlabial space of a wearer as defined above will require placement between the inside surfaces of the labia majora without regard to the precise location of the boundary between the labia majora and the labia minora for a particular wearer. For a more detailed description of this portion of the female anatomy, attention is directed to *Gray's Anatomy*, Running Press 1901 Ed. (1974), at 1025–1027.

The term "toilet-disposable" as used herein includes the following characteristics of an absorbent interlabial device: flushability, dispersibility, and biodegradability. As used herein the terms "flushable" and "flushability" refer to a product's ability to pass though typically commercially available household toilets and plumbing drainage systems without causing clogging or similar problems that can be directly associated with the physical structure of the product. It is recognized, however, that there can be many differences between the various types of toilets available. Therefore, for the purposes of the appended claims, a test to determine the flushability of a catamenial product, such as an absorbent interlabial device, is set out in the TEST METHODS section of this specification.

The term "dispersible" as applied herein to an absorbent interlabial device refers to an article which will disperse into at least two fragments in mildly agitated water. Such a device will break into pieces in a conventional toilet and/or domestic plumbing system, and will ultimately be effectively processed though a sewage treatment system.

The term "biodegradable" as used herein refers to an absorbent device which is preferably at least partially constructed of biodegradable materials.

The absorbent interlabial device 20 shown in FIG. 1 has a longitudinal centerline L which runs along the "x" axis shown in FIG. 1. The term "longitudinal", as used herein, refers to a line, axis or direction in the plane of the interlabial device 20 that is generally aligned with (e.g., approximately parallel to) a vertical plane which bisects a standing wearer into left and right body halves when the interlabial device 20 is worn. The terms "transverse," "lateral," or "y direction" as used herein, are interchangeable, and refer to a line axis or direction that is generally perpendicular to the longitudinal direction. The lateral direction is shown in FIG. 1 as the "y" direction. The "z" direction, shown in FIG. 1, is a direction parallel to the vertical plane described above. The term "upper" refers to an orientation in the z-direction toward the wearer's head. "Lower" or downwardly is toward the wearer's feet.

As shown in FIG. 1, the interlabial device 20 comprises a central absorbent portion (or "main absorbent portion") 22, and a pair of flexible extensions 24 joined to the central absorbent portion 22. The central absorbent portion 22 should be at least partially absorbent. The central absorbent portion 22 may comprise non-absorbent portions, such as a liquid impervious barrier to prevent absorbed exudates from leaking out of the main absorbent portion 22. The central absorbent portion 22 comprises an upper portion 26 and a lower portion 28 that is opposed to the upper portion. The flexible extensions 24 are joined to the upper portion 26 of the central absorbent portion. In use, the upper portion 26 is positioned furthest inward into the wearer's interlabial space.

The interlabial device 20 should be of a suitable size and shape that allows at least a portion thereof to fit comfortably within the wearer's interlabial space and to cover the wearer's vaginal orifice, and preferably also the wearer's urethra. The interlabial device 20 at least partially blocks, and more preferably completely blocks and intercepts the flow of menses, urine, and other bodily exudates from the wearer's vaginal orifice and urethra.

The size of the interlabial device 20 is also important to the comfort associated with wearing the device. In the preferred embodiment shown in FIG. 1, the main absorbent portion 22 of the interlabial device 20 has a length as measured along the longitudinal centerline, L, of between about 35 mm and about 120 mm. Preferably, the length of the interlabial device 20 is between about 45 mm and about 55 mm, and more preferably, is about 49 mm. The caliper (or width) of the central absorbent portion 22 of the interlabial device as measured in the transverse direction (or "y"-direction) is preferably less than or equal to about 8 mm, more preferably the caliper is between about 3 mm and about 8 mm, most preferably, the caliper is about 4.5 mm. Caliper measurements given herein were measured using an AMES gage with a 0.25 psi (gauge) load and a 0.96 inch diameter foot. Those skilled in the art will recognize that if a 0.96 inch diameter foot is not appropriate for a particular sample size, the foot size may be varied while the load on the gauge is accordingly varied to maintain a confining pressure of 0.25 psi (gauge). The height (or "z"-direction dimension) of the main absorbent portion 22 is preferably between about 8 mm and about 35 mm, and more preferably is about 20 mm.

The interlabial device 20 is preferably provided with sufficient absorbency to absorb and retain the exudates discharged from the wearer's body. The capacity of the product, however, is dependent at least partially upon the physical volume of the absorbent interlabial device 20, particularly the central absorbent portion 22 thereof. The central absorbent portion 22 preferably has a capacity of at least about 1 g of 0.9% by weight saline solution, and may have a capacity of up to about 30 g by using absorbent gels or foams that expand when wet. Capacities may typically range from about 2 to about 10 grams, for saline. Those skilled in the art will recognize that the capacity for absorption of body exudates such as menses will typically be smaller than the capacities given above for absorption of saline. A method for measuring absorbent capacity is described in the TEST METHODS section, below. Since the interlabial space can expand, larger volumes can be stored in the interlabial space, if the fluid is stored as a gel, which adjusts to the body pressures. Additionally, if the absorbent interlabial device 20 does not reside completely within the wearer's interlabial space, some of the absorbed exudates may be stored externally to the wearer's interlabial space.

Figures 2, 3, 4, 5:
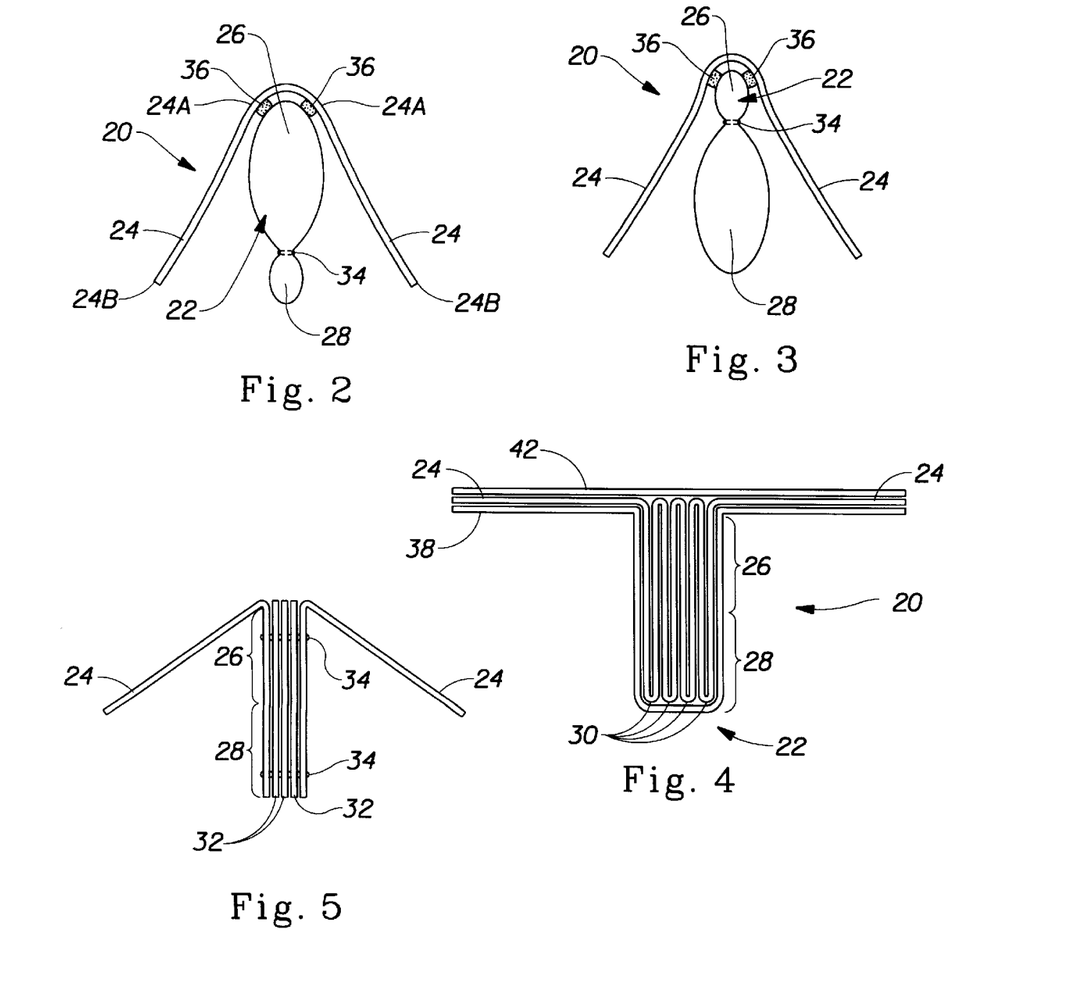
FIG. 2 is an end view of the absorbent device shown in FIG. 1.
FIG. 3 is an end view of a variation of the preferred embodiment shown in FIG. 2.
FIG. 4 is an end view of an alternative preferred embodiment of the present invention having a pleated central absorbent portion.
FIG. 5 is an end view of an alternative preferred embodiment of the present invention showing a central absorbent portion having a multiple layer structure.

The central absorbent portion 22 of the preferred embodiment shown in FIGS. 1–3 may comprise any suitable type of absorbent structure that is capable of absorbing and/or retaining liquids (e.g. menses and/or urine). The central absorbent portion 22 may be manufactured in a wide variety of shapes. Non-limiting examples include ovoid, trapezoidal, rectangular, triangular, cylindrical, hemispherical or any combination of the above. The central absorbent portion 22 may, likewise, be manufactured and from a wide variety of liquid-absorbent materials commonly used in absorbent articles. Suitable materials include materials such as comminuted wood pulp which is generally referred to as airfelt. Examples of other suitable absorbent materials include cotton fibers or cotton lintels; creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers (in granular or fiberous forms); absorbent gelling materials; or any equivalent material or combinations of materials, or mixtures of these. Preferred absorbent materials comprise cotton batts, folded tissues, woven materials, nonwoven webs, needle punched rayon, and thin layers of foam. The central absorbent portion 22 may comprise a single material or a combination of materials, such as a wrapping layer surrounding a central wadding comprised of a different absorbent material.

The central absorbent portion 22 preferably at least partially comprises biodegradable materials. As used herein, the term "biodegradable materials" refers to a material having greater than or equal to about 70% biodegradation (percentage of theoretical carbon dioxide evolution) after 28 days when measured according to the Sturm Test which has been designated Method 301B by the Organization for Economic Cooperation and Development. Preferably, the materials comprising the present invention have a biodegradation of greater than about 80% and, more preferably, biodegradation is greater than or equal to about 90%.

While biodegradable materials are preferred for the flushable absorbent interlabial device 20, it is not necessary that each and every material used be biodegradable. For example, the device 20 may comprise superabsorbent particles which do not biodegrade, and this will not affect the ability of the overall device 20 to remain toilet-disposable and to be effectively processed in a sewage treatment system.

Product integrity during wear is attained by recognizing that the shearing motion of the labia during walking does not exert large forces on a product within the labia. Therefore, soft materials or those with a lower wet strength can provide sufficient integrity to prevent degradation during wear, while still allowing disintegration in the toilet. Another feature of this invention is that the surface of the main absorbent portion 22 will be protected by the flexible extensions 24. Therefore, softer or lower strength materials may be used in the central absorbent portion 22 while the flexible extensions 24 may be constructed of higher strength materials to protect the central absorbent portion 22 from fragmenting within the wearer's interlabial space. In the preferred embodiment shown in FIG. 1, the central absorbent portion 22 is formed of a soft absorbent material such as rayon fibers or other suitable natural or synthetic fibers or sheeting. Superabsorbent polymers may be added to such soft absorbent material.

The central absorbent portion 22 shown in FIG. 1 is generally of an ovoid cross sectional shape as shown in FIG. 2. The central absorbent portion 22 of the embodiment shown in FIGS. 1 and 2 comprises an upper portion 26 with a larger transverse sectional dimension relative to that of the lower portion 28. The upper portion 26 is preferably integral with the lower portion 28. In less preferred embodiments, however, the upper portion 26 and lower portion 28 may comprise separate elements joined together by any suitable means know in the art. In the preferred embodiment shown in FIGS. 1 and 2, the juncture of the upper portion 26 and lower portion 28 of the central absorbent portion 22 comprises a substantially abrupt change in the transverse dimension thereby forming a shoulder-like configuration at such juncture. In the preferred embodiment shown in FIGS. 1 and 2, the juncture of the upper portion 26 and lower portion 28 of the central absorbent portion 22 is formed by stitching 34.

In a variation of the preferred embodiment described above and shown in FIGS. 1 and 2, the upper portion 26 may have a smaller transverse sectional dimension relative to the transverse sectional dimension of the lower portion 28. An absorbent interlabial device 20 having such a configuration is shown in FIG. 3.

The central absorbent portion 22 can be made by any suitable process. U.S. Pat. No. 4,995,150 issued to Gerstenberger et al. on Feb. 26, 1991 and U.S. Pat. No. 4,095,542 issued to Hirshman on Jun. 20, 1978 describe methods for making absorbent devices which are suitable for use as the central absorbent portion 22 of the absorbent interlabial device 20 shown in FIGS. 1–3.

As shown in FIGS. 1–3, the absorbent interlabial device 20 may also comprise a pair of flexible extensions 24 which are joined to the upper portion 26 of the central absorbent portion 22 of the absorbent interlabial device 20. Preferably, the flexible extensions 24 comprise a biodegradable material. Additionally, the flexible extensions 24 preferably will detach from the central absorbent portion 22 when the absorbent interlabial device 20 is immersed in mildly agitated room temperature water. More preferably, the flexible extensions 24 will fragment into a plurality of pieces in addition to detaching from the main absorbent portion 22 when the absorbent interlabial device 20 is immersed in mildly agitated room temperature water.

In the preferred embodiment shown in FIGS. 1–3, the flexible extensions 24 are generally rectangular in shape. Other shapes are also possible for the flexible extensions 24 such as semi-circular, trapezoidal, or triangular. The flexible extensions 24 preferably are from about 30 mm to about 160 mm in length, more preferably from about 45 mm to about 130 mm in length, and most preferably from about 50 mm to about 115 mm in length. While the flexible extensions 24 can have a length (measured in the x-direction) which is shorter or longer than the central absorbent portion 22, preferably they have a length which is about 25 mm or longer. The width of each flexible extensions refers to the distance from the attachment of flexible extension 24 to the central absorbent portion 22 (or the proximal end 24A of the flexible extension 24) to the distal end (or free end) 24B of the flexible extension 24. The width of the flexible extensions 24 is preferably about equal to or less than the height of the central absorbent portion 22 as described above. The caliper of the flexible extensions is preferably less than or equal to about 3 mm, more preferably less than or equal to about 2 mm, and most preferably less than or equal to about 1 mm. Ideally the caliper of the flexible extensions 24 and the central absorbent portion 22 are selected such that the caliper of the overall absorbent interlabial structure 20 is less than or equal to about 8 mm.

The flexible extensions 24 may be constructed of a tissue layer. A suitable tissue is an airlaid tissue available from Fort Howard Tissue Company of Green Bay, Wis., and having a basis weight of 35 lbs./3000 sq. ft. Another suitable airlaid tissue is available from Merfin Hygenic Products, Ltd., of Delta, British Columbia, Canada, having a basis weight of 61 $g/m^2$ and having the designation grade number 176. Preferably, these tissues are coated with a layer of nonwoven material which is heat sealed to the body-contacting side of the tissue to help prevent the tissue layer from fragmenting in the labia. A suitable nonwoven material is known as COROLIND and is available from Corovin, GmbH, Peine, Germany. The flexible extensions 24 may also optionally be backed with a layer of material which is impervious or semi-pervious to body exudates such as, polyvinylalchohol. The flexible extensions 24 may also be backed or coated with a polyethelyne film which may be applied as a laminate or extruded onto the flexible extensions 24.

In the preferred embodiments shown in FIGS. 1–3 the pair of flexible extensions 24 may comprise a single sheet of material extending to either side of the longitudinal centerline L of the central absorbent portion 22 of the absorbent interlabial device 20. Alternatively, the pair of flexible extensions 24 may comprise separate sheets of material independently joined to the upper portion 26 of the central absorbent portion 22. Preferably, the flexible extensions 24 are arranged symmetrically about the longitudinal centerline L of the central absorbent portion 22. The flexible extensions 24 are joined to the upper portion 26 of the central absorbent portion 22 of the absorbent interlabial device 20. Most preferably, the flexible extensions are joined to the top surface of the upper portion 26 of the central absorbent portion 22, or within about 3 mm of the top surface of the central absorbent portion 22.

The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element; i.e., one element is essentially part of the other element.

The flexible extensions 24 may be joined to the upper portion 26 of the central absorbent portion 22 by any variety of means. For example, in the preferred embodiments shown in FIGS. 1–3 the flexible extensions 24 may be joined to the upper portion 26 using any suitable adhesive 36 centered about the longitudinal centerline L of the central absorbent portion 22 (i.e., on opposite sides of the longitudinal centerline L). The adhesive 36 may extend continuously along the length of the central absorbent portion 22 or it may be applied in a "dotted" fashion at discrete intervals. Alternatively, the flexible extensions 24 may be joined to the upper portion 26 of the central absorbent portion 22 by stitching (such as with cotton or rayon thread), thermally bonding, fusion bonding, or any other suitable means known in the art for joining such materials. The flexible extensions 24 may be joined to the central absorbent portion 22 using a water soluble adhesive or by being stitched using a water soluble thread. These forms of attachment enhance the ability of the flushable absorbent interlabial device 20 to disperse in mildly agitated room temperature water, thereby enhancing toilet-disposability.

Figure 9:
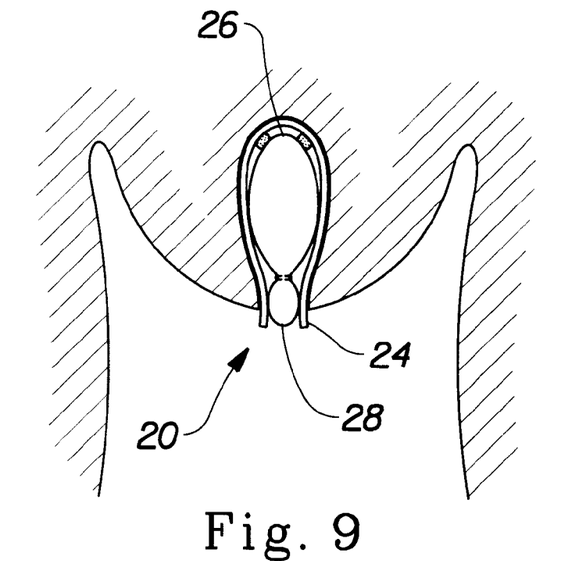
FIG. 9 is a cross-sectional view of the same region of the wearer's body shown in FIG. 6 showing how the absorbent interlabial device of the present invention fits when the wearer is standing.

As shown in FIGS. 1–3, the flexible extensions 24 are attached to the upper portion 26 of the central absorbent portion 28. The flexible extensions 24 extend downwardly and outwardly from the central absorbent portion 22 to a free end 24B which is unattached to the central absorbent portion. The flexible extensions 24 may be biased slightly outward from the central absorbent portion 22 so as to tend to keep the extensions 24 in contact with the inner surfaces of the labia when the absorbent interlabial device 20 is in place. Additionally, the naturally moist surfaces of the labia will have a tendency to adhere to the material comprising the flexible extensions 24 further tending to keep them in contact with the inner surfaces of the labia. Preferably, the flexible extensions 24 should be capable of motion from a position where the free ends of the flexible extensions 24 lie adjacent to the central absorbent portion 22 (as shown in FIG. 9) to a position where the flexible extensions 24 extend directly out from the central absorbent portion 22 in the transverse direction (as shown in FIG. 4).

Figure 8:
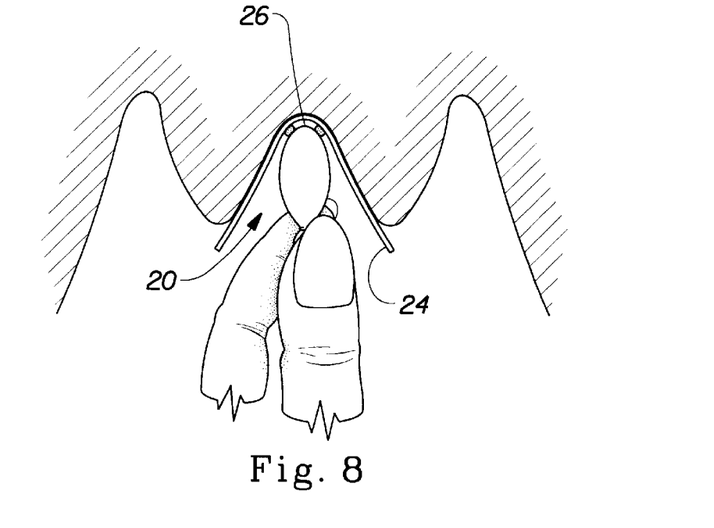
FIG. 8 is a cross-sectional view of the same region of the wearer's body shown in FIG. 7 showing the flexible extensions of the present invention covering the wearer's fingertips as the absorbent device of the present invention is inserted into the wearer's interlabial space.

The flexible extensions 24 should be of sufficient width and flexibility to allow the flexible extensions to cover the wearer's fingertips as the absorbent interlabial device 20 is inserted into the wearer's interlabial space. FIG. 8 shows how a wearer may grasp the central absorbent portion 22 of the absorbent interlabial device 20 while the flexible extensions 24 remain between the wearer's fingers and her body as the device 20 is inserted. Additionally, the flexible extensions 24 should be capable of moving with the inner surfaces of the wearer's labia to maintain contact with the same. The flexible extensions 24 help keep the central absorbent portion 22 in place throughout a range of wearer motions such as squatting.

The flexible extensions 24 may be either absorbent or non-absorbent. Preferably, the flexible extensions 24 have at least some absorbency. The flexible extensions 24 may have a greater absorbent capacity than the absorbent capacity of the central absorbent portion 22. The flexible extensions 24 may be as hydrophilic as the central absorbent portion 22 or less hydrophilic than the central absorbent portion 22. In one embodiment, the flexible extensions 24 may be treated to make them less hydrophilic than the central absorbent portion 22. That is, the flexible extensions 24 may have an advancing contact angle greater than the advancing contact angle of the central absorbent portion 22, such that fluid is preferentially directed toward and absorbed by the central absorbent portion 22. Preferably, the majority of the fluid absorbed and retained by the absorbent interlabial device 20 will ultimately be retained in the central absorbent portion 22. For a more detailed description of hydrophilicity and contact angles see the following publications which are incorporated by reference herein: The American Chemical Society Publication entitled "Contact Angle, Wettability, and Adhesion," edited by Robert F. Gould, and copyrighted in 1964; and TRI/Princeton Publications, Publication Number 459, entitled "A Microtechnique for Determining Surface Tension," published in April 1992, and Publication Number 468 entitled, "Determining Contact Angles Within Porous Networks," published in January, 1993, both edited by Dr. H. G. Heilweil.

The stiffness of both the central absorbent portion 22 and the flexible extensions 24 is important for product comfort. If the central absorbent portion 22 is too flexible, the device is not conveniently or easily placed between the folds of the labia, if it is too stiff, the device is uncomfortable and when the user is in a sitting position, the product can be forced forward against the clitoris causing discomfort. The central absorbent portion 22 preferably has a stiffness approximately equal to that of the products described in U.S. Pat. Nos. 4,995,150 and 4,095,542.

The strength and stiffness of the flexible extensions 24 are important characteristics of their design. If the flexible extensions 24 have a wet burst strength of about less than or equal to 15 grams, they will tend to shred and may leave pieces remaining in the wearer's interlabial space. Similarly, if the flexible extensions 24 are as stiff as a manila file folder, they do not provide sufficient flexibility to dynamically adjust to the motion of the labia. The stiffness of the flexible extensions is measured as a bending resistance. Preferably, the flexible extensions 24 have a bending resistance of less than about 25 gm measured using the Three Point Bend Test. More preferably, the flexible extensions 24 have a bending resistance of less than or equal to about 5 gm. A description of the Three Point Bend Test is contained in the TEST METHODS section, below. The flexible extensions 24 also have an inherent strength, so that during application and wear they do not tear and serve to protect the main absorbent portion 24. The wet strength for the flexible extensions should exceed 15 grams, and preferably exceeds 150 grams, and most preferably exceeds 300 grams. The wet strengths given above are measured using the Wet Burst Test which is described in greater detail in the TEST METHODS section, below.

Preferably, the toilet-disposable interlabial absorbent device 20 of the present invention will disperse into at least two fragments within two hours of exposure to mildly agitated room temperature water as described in the Water Dispersion Test in the TEST METHODS section, below. More preferably, the flushable interlabial absorbent device 20 will be dispersed into a plurality of fragments within about 60 minutes or, even more preferably within about 30 minutes and most preferably, within about 15 minutes as measured by the Water Dispersion Test. Preferably, the product will break into fragments which are smaller than about 6 $in^2$, more preferably smaller than about 2 $in^2$, most preferably smaller than about 1.5 $in^2$. In particularly preferred embodiments of the present invention, each of the components of the flushable interlabial absorbent device 20 will disperse into a plurality of fragments when immersed in mildly agitated water. Alternatively, the components of the absorbent interlabial device 20 may separate from each other without themselves breaking into a plurality of fragments (e.g. the flexible extensions 24 may break apart from the central absorbent portion 22 while each otherwise remains intact).

In an alternative preferred embodiment shown in FIG. 4, the central absorbent portion 22 of the absorbent interlabial device 20 comprises a pleated structure. As shown in FIG. 4, the central absorbent portion 22 comprises a folded tissue web. The folded tissue web preferably has a strength greater than that of standard non-wet strength toilet tissue. Preferably, the central absorbent portion 22 comprises a tissue having a temporary wet strength of greater than or equal to about 100 g. In a preferred design this wet strength will decay to about 50% or less of the original strength over about 30 minutes.

As shown in FIG. 4, the tissue web comprising the central absorbent portion 22 is folded into a pleated structure comprising a plurality of pleats 30 that are arranged in a laterally side-by-side relationship. The tissue web can be folded so that it has any suitable number of pleats. Preferably, the tissue web is folded so that the overall caliper (i.e., the width) of the central absorbent portion 22 of this embodiment is between about 2 mm and less than or equal to about 7 mm.

The pleats in the folded tissue web are preferably connected or joined (or retained) in some suitable manner so that the pleated sections maintain their pleated configuration, and are not able to fully open. The pleats can be connected by a variety of means including the use of thread, adhesives, or heat sealing tissues such as the Merfin tissue discussed above. A preferred design uses stitching which joins all of the pleats in the central absorbent portion 22 together. Preferably, the central absorbent structure 22 is provided with five stitch locations (four at the corners and one additional location approximately midway between the two lower corners). The thread used for this stitching may be water soluble to enhance the ability of the device 20 to disperse in a toilet.

In a variation of the pleated structure shown in FIG. 4, the central absorbent portion 22 may comprise a single fold or pleat. The space between the two sides of the once folded central absorbent portion 22 may be oriented in either the upward or downward direction when inserted into the wearer's interlabial space.

The pleated structure of the central absorbent portion 22 provides several advantages. One advantage provided by the pleated structure is that exudates can penetrate into the pleats of the structure which present a larger and more effective absorbent surface for acquisition than a flat surface. This is particularly important when dealing with potentially viscous fluids and particulate material such as cellular debris and clots which can plug the surface of the structure presented to the body. A second advantage of this design is that the caliper (or width) of the product can be easily and conveniently controlled by varying the number of pleats. The structure shown in FIG. 4 also provides a convenient central zone for grasping the product and inserting into the labia, while the body/fingers on the inserting hand are protected from contacting the wearer's body.

As noted above for the preferred embodiment shown in FIGS. 1–3, the flexural rigidity of the central absorbent portion 22 is also important for product comfort with the pleated structure shown in FIG. 4. An advantage of the pleated structure is that the number, thickness, and tightness of the pleats control the stiffness of the structure.

The preferred embodiment shown in FIG. 4, preferably has central absorbent portion 22 and flexible extension 24 dimensions similar to those described above for the embodiment shown in FIGS. 1–3. The width of the central absorbent portion 22 of the interlabial device 20 as measured in the transverse direction (y-direction) is preferably between about 2 mm and less than or equal to about 7 mm. Preferably, in a preferred embodiment, the width of the central absorbent portion 22 of the interlabial device 20 is about 4.5 mm. As shown in FIG. 4, where the central absorbent portion 22 is of a uniform transverse dimension (i.e., there is no abrupt change in transverse dimension defining the juncture between the upper portion and lower portion) the division between the upper portion 26 and lower portion 28 is considered to be at a height equal to about one-half of the total height of the central absorbent portion 22.

The pleated design shown in FIG. 4 has the additional benefit of easily providing the flexible extensions 24. The extensions 24 can comprise the same material as the central absorbent portion 22, or they can comprise a different material. The extensions 24 are joined to the upper portion 26 of the central absorbent portion 22, and most preferably, for this embodiment, are joined to the top surface of the central absorbent portion 22, or within 3 millimeters of the top surface of the central absorbent portion 22. Preferably, in the embodiment shown in FIG. 4, the extensions 24 are integral portions of the central absorbent portion 22 (that is, the extensions 24 comprise integral extensions of the absorbent tissue material that is folded to form the central absorbent portion 22.

The central absorbent portion 22 and the flexible extensions 24 of the absorbent interlabial device 20 shown in FIG. 4 may be constructed from any of the materials previously discussed for the embodiments shown in FIGS. 1–3.

The embodiment shown in FIG. 4 can be provided with various optional features. For example, there may be spacers or high loft or void zones between the pleats to improve the ability of the device 20 to move exudates downward. Additionally, the pleats on the portion of the product contacting the pelvic floor do not need to be of uniform height. For example, the pleated material in the center might be higher and, therefore, easily collapsed under pressure. Such an arrangement can provide better fit and/or comfort.

In another variation of the pleated structure shown if FIG. 4, the central absorbent portion 22 may comprise a plurality of individual layers 32 joined in a face-to-face relationship. Such a device is shown in FIG. 5. The structure shown in FIG. 5 may have all of the same characteristics described above for the pleated structure. In one embodiment, each of the individual layers 32 may be comprised of a permanent wet strength tissue held together by water soluble thread or adhesive. Alternatively, the individual layers 32 may themselves disperse in a toilet in addition to separating from each other. One additional benefit of the use of a plurality of individual layers 32 is that the various layers may comprise different materials with different properties or characteristics. Each of the flexible extensions 24 may be integral with one of the individual layers 32 or may be joined separately to the upper portion 26 of the main absorbent portion 22. Preferably, the individual layers 32 are arranged in a side-by-side relationship so that the spaces between the layers are oriented in the z-direction (as shown in FIG. 5).

The interlabial device 20 in any of the embodiments shown in the drawings may comprise other optional components. For example, the interlabial device 20 may comprise a topsheet 42 positioned over and joined to all or a portion of the body facing surface of the device 20 and/or a backsheet 38 positioned over and joined to all or a portion of its back surface, including the flexible extensions 24. If a topsheet 42 and/or a backsheet 38 are used, these components are preferably dispersible in mildly agitated room temperature water.

If the optional topsheet 42 and/or backsheet 38 do not themselves fragment in mildly agitated room temperature water, they should not inhibit the ability of the remainder of the absorbent interlabial device 20 to disperse into at least two fragments when so exposed to mildly agitated room temperature water. For example, the topsheet 38 or backsheet 42 material may detach from the remainder of the device 20 in mildly agitated room temperature water. Alternatively, the topsheet 28 or the backsheet 42 may comprise a plurality of independent sections which are not directly attached to each other, but which are separately attached to the central absorbent portion 22 and/or the flexible extensions 24 of the absorbent interlabial device 20 so that the components of the device 20 can freely separate from each other.

Preferably, if a topsheet 42 and/or a backsheet 38 is used, these components are joined to at least a portion of the central absorbent portion 22. In an alternative embodiment, the central absorbent portion could be at least partially wrapped by a topsheet 42.

If a topsheet is used, the topsheet should be compliant, soft feeling, and non-irritating to the wearer's skin. Further, the topsheet should be liquid pervious permitting liquids (e.g., menses and/or urine) to readily penetrate through its thickness. A suitable topsheet may be manufactured from a wide range of materials such as woven and nonwoven materials including natural fibers (e.g., wood or cotton fibers), synthetic fibers, or from a combination of natural and synthetic fibers.

Preferred materials for the topsheet 42 of the present invention include nonwoven webs of cotton and nonwoven webs of rayon either of which may be blended with polypropylene. In a preferred embodiment of the present invention, the body surface of the topsheet is hydrophilic so as to help liquid to transfer through the topsheet faster than if the body surface was not hydrophilic so as to diminish the likelihood that menstrual fluid or other bodily discharges will flow off the topsheet 42 rather than flowing into and being absorbed by the central absorbent portion 22. The body surface of the topsheet 42 can be made hydrophilic by treating it with a surfactant such as is described in U.S. Pat. No. 4,950,254 issued to Osborn.

If a backsheet is used, the backsheet could be impervious or semi-pervious to liquids (e.g., menses and/or urine) and is preferably flexible. As used herein, the term "flexible" refers to materials which are compliant and will readily conform to the general shape and contours of the human body. The backsheet prevents the exudates absorbed and contained in the main absorbent portion 22 from wetting articles which contact the absorbent interlabial device 20 such as the wearer's body or undergarments. Additionally, use of the backsheet may provide an improved surface for the wearer to grasp between the fingers as the absorbent interlabial device 20 is inserted, or as the device is optionally removed with the fingers.

The backsheet 38 may comprise a woven or nonwoven material, polymeric film such as polyvinylalchohol, or composite materials such as a film-coated nonwoven material. Preferably, the backsheet 38 is a polyvinylalchohol film having a thickness of from about 0.012 mm (0.5 mil) to about 0.051 mm (2.0 mils).

As previously discussed, the absorbent interlabial device 20 of the present invention is preferably designed to be placed entirely within the interlabial space of a wearer. To use the absorbent interlabial device 20 of the present invention, the wearer holds the central absorbent portion 22 between her fingers. As shown in FIG. 8, the flexible extensions 24 are spread apart so as to cover the tips of the wearer's fingers during insertion. This feature provides for a hygenic insertion of the absorbent interlabial device 20 of the present invention. The upper portion 26 is inserted first and furthest into the interlabial space. The wearer may assume a squatting position during insertion to assist in spreading the labial surfaces. Once the absorbent interlabial device 20 is inserted, the flexible extensions 24 tend to adhere to the inside surfaces of the labia. When the wearer is standing, the labial walls close more securely around the absorbent interlabial device 20 as shown in FIG. 9.

The interlabial device 20 is preferably at least partially retained in place by exerting a slight laterally outwardly-oriented pressure on the inner surfaces of the wearer's labia minora, labia majora, or both. Additionally, the product is also held by attraction of naturally moist labial surfaces to the tissue comprising the flexible extensions 24. Optionally, the flexible extensions 24 may be provided with a biocompatible adhesive to assist the adhesion of the flexible extensions 24 to the inside surfaces of the wearer's labia. The strength of such an adhesive should be selected to assist the absorbent interlabial device 20 in staying in place, while still allowing for reliable, and comfortable removal of the device from the wearer's interlabial space. Examples of suitable adhesives are described in U.S. Pat. No. 5,336,208 issued to Rosenbluth et al.

Figure 6:
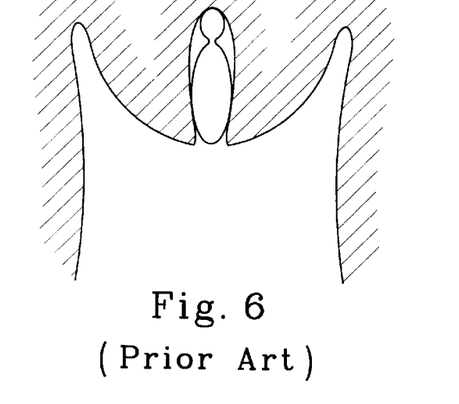
FIG. 6 is a cross-sectional view of a wearer's body surrounding and including the wearer's labia majora and labia minora showing how a prior art interlabial device might fit in the space between the wearer's labia when the wearer is standing.
Figure 7:
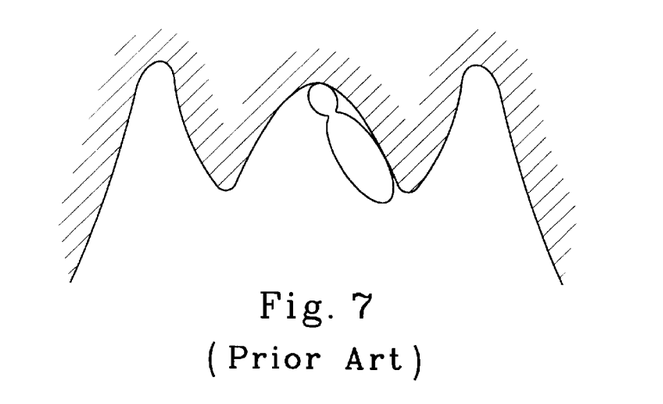
FIG. 7 is a cross-sectional view of the same region of the wearer's body shown in FIG. 6 showing how the prior art device might fit when the wearer squats.
Figure 10:
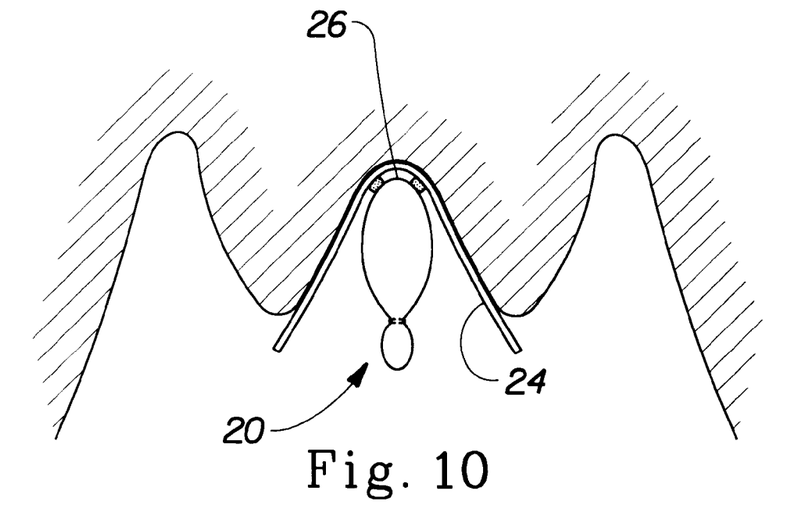
FIG. 10 is a cross-sectional view of the same region of the wearer's body shown in FIG. 7 which shows how the absorbent interlabial device of the present invention fits when the wearer squats.

The absorbent interlabial device 20 is believed to differ from the prior art in a number of respects. FIG. 6 shows a prior art interlabial device positioned within the interlabial space when the wearer is standing. When the wearer squats, however, the labia tend to separate as shown in FIGS. 7 and 10. The prior art device may tend to shift to one side or another in such a situation (as shown in FIG. 7). If the wearer urinates when the prior art device is in the position shown in FIG. 7, the stream of urine will completely miss the device. The flexible extensions 24 of the present invention, however, are adapted to maintain contact with the inside surfaces of the labia in order to keep the absorbent interlabial device 20 in proper position (as shown in FIG. 10). This action of the flexible extensions 24 is believed to keep the absorbent interlabial device 20 of the present invention in a position which more consistently blocks the orifice of the urethra than the prior art device. As a result, the absorbent interlabial device 20 of the present invention is believed to be expelled by urination more reliably than the prior art device. As noted previously, the flexible extensions 24 also cover the wearer's fingertips during insertion (as shown in FIG. 8) thereby providing for a more hygienic insertion than is achieved with the prior art device. Optionally, the absorbent interlabial device 20 may be removed by grasping the lower portion 28 of the central absorbent portion 22 with the fingers. Again, the flexible extensions 24 continue to cover the fingertips thereby allowing for a more hygienic removal of the absorbent interlabial device 20 than is achieved with the prior art device.

The absorbent interlabial device 20 can be worn as a "stand alone" product for protection from menstrual, incontinent, or vaginal discharges. Alternatively, it can be worn as a back up to a tampon, or in combination with a sanitary napkin, pantiliner, or incontinence pad for menstrual or incontinence use. If the absorbent interlabial device 20 is used with a sanitary napkin, the sanitary napkin can be of any thickness. Use with a sanitary napkin may be preferred at night to reduce rear soiling. The interlabial device 20 can be worn in conventional panties, or it can be used with menstrual shorts. The absorbent interlabial device 20 of the present invention may be provide with absorbent gelling material (AGM) either in a particulate or fibrous form.

Numerous alternative embodiments of the absorbent interlabial device of the present invention are possible. For example, these products are designed to be removed by urination, although an alternative extraction string or loop may be used. These products may also be used with medicinal treatments. These products are designed to fragment in water with agitation and are constructed of materials which are biodegradable. These features, combined with their size allow for disposable by flushing in a conventional toilet. The absorbent interlabial device 20 may also be constructed with a plurality of slits in the central absorbent portion 22 so as to permit bending of the product in multiple independent directions. Such a structure allows the product to more easily respond to the stresses associated with body movements. In a preferred version of the embodiment shown in FIG. 4, the ends of the surface of the central absorbent facing away from the body may be rounded to reduce the force on the product during sitting. The top surface or side edges of the structure may have one or more slits or have other regions of preferred bending so that product may easily adjust to the vertical pressure against the pelvic floor, to help accommodate the non-linear surface of the pelvic floor between the clitoris and the perineum. The flexible extensions 24 of the absorbent devices above may also act as a spring in both wet and dry conditions such that the sides of the product tend to expand outward pressing against the lateral walls of the labial vestibule, thereby, holding the product in place. In addition, it is preferred that the flexible extensions 24 maintain the ability to act as a "spring" when wet, such as when the product is saturated with liquid. Structures, such as polyurethane foams can provide these properties.

Test Methods

Absorbent Capacity

Absorbent capacity may be determined as follows. The test is performed on samples that have been conditioned by leaving them in a room at 50% relative humidity and at 73 F. for a period of two hours prior to the test. The test should be performed under similar conditions.

The article is weighed to the nearest 0.1 gram. The article is then submerged in a beaker of sterile 0.9% saline solution (obtainable from the Baxter Travenol Company of Deerfield, Ill.), such that the article is totally submerged and is not bent or otherwise twisted or folded. The article is submerged for 10 minutes. The article is removed from the saline and suspended for two minutes in a vertical position to allow the saline to drain out to the article. The article is then placed body facing surface down onto an absorbent blotter, such as the filter paper #631 available from the Filtration Science Corp., Eaton-Dikeman Division of Mount Holly Springs, Pa. A uniform 17.6 grams per square centimeter load is placed over the article to squeeze excess fluid out. The absorbent blotter is replaced every 30 seconds until the amount of fluid transferred to the absorbent blotter is less than 0.5 grams in a 30 second period. Next, the article is weighed to the nearest 0.1 gram and the dry weight of the article is subtracted. The difference in grams is the absorbent capacity of the article.

Three Point Bend Test

The Three Point Bend Test is performed on samples that have been conditioned by leaving them in a room at 50% relative humidity and at 73° F. for a period of two hours prior to the test. The test should be performed under similar conditions.

Figure 11:
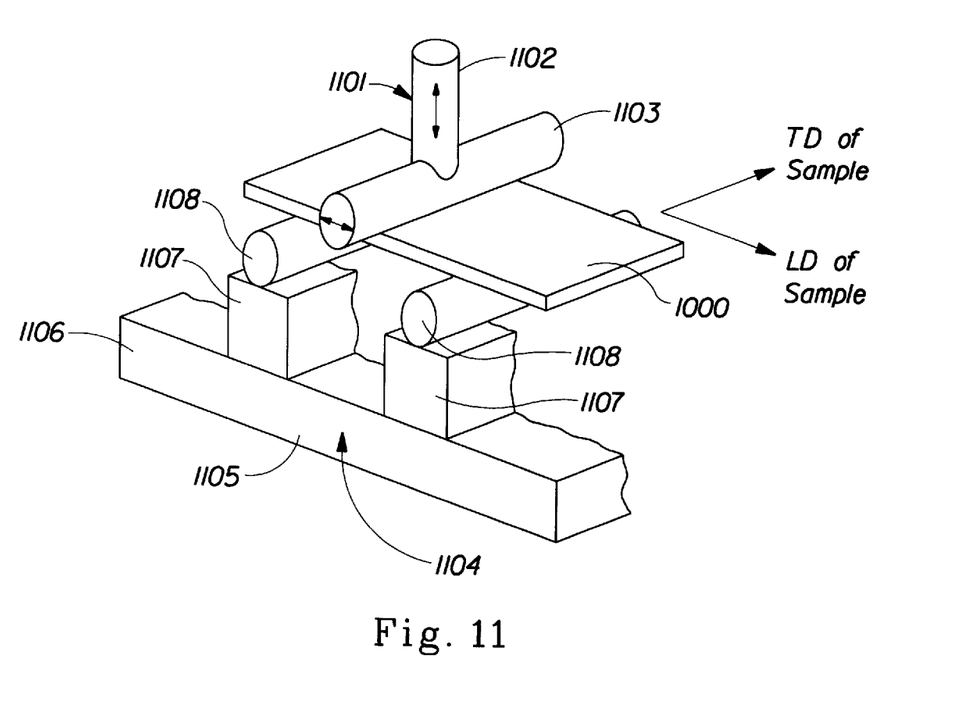
FIG. 11 is a schematic perspective view of the Three Point Bend Test apparatus.

The three point bend test uses an INSTRON Model 4502 tensile and compression testing machine, which is available from Instron Corporation of Canton, Mass. The test also uses a special displacement "T-rod" and a special test sample holder. As shown in FIG. 11, the "T-rod" 1101 comprises a pair of 6.40 mm diameter metal rods perpendicularly mounted together. The drive rod 1102 is about 125 mm long and the push rod 1103 is about 75 mm long. Preferably, the end of the drive rod 1102 is tapered to fit the circumference of the push rod 1103 and the two are glued, welded and/or screwed to each other. The opposite end of the drive rod 1102 is mounted to the crosshead unit of the INSTRON machine. The test sample holder 1104 comprises a fixture base 1105 for positioning and supporting a pair of supporting rods 1108. The fixture base 1105 comprises a base 1105 and two rectangular supports 1107 mounted in parallel on the base 1106. The base 1106 and the supports 1107 are each preferably made of LEXAN (plexiglas) plate of about 10 mm to about 13 mm thickness. A supporting rod 1108 of the same materials as the "T-bar" and about 150 mm long is mounted on each support 1107 of the fixture base 1105. The supporting rods 1108 are mounted so as to leave 10 mm of open space between them (measured at the point on each rod which is closest to the other). As shown in FIG. 11, the "T-rod" 1101 is centered between the supporting rods 1108.

The INSTRON machine is set for a crosshead speed of 2.0 in/min (50.8 mm/min). The INSTRON machine is set up so that the crosshead unit will travel 10 mm down and back for each sample tested.

Prior to testing of a sample, the T-rod 1101 is lowered until it is resting directly on top on one of the supporting rods 1108. The vertical position of the T-rod 1101 is "zeroed" when the load as it rests on supporting rod 1108 is about 1gram$_f$. The T-rod 1101 is then raised 5 mm from this zero position and centered between both supporting rods 1108.

The sample 1000 to be tested is a piece of material taken from one of the flexible extensions. The sample 1000 taken from the side wrapping elements should have a dimension of about 25 mm in the longitudinal direction LD and a dimension in the transverse direction of a about 10 mm. The sample is placed so that the push rod 1103 is running parallel to a side of the sample that was oriented in the transverse direction TD.

The T-rod 1101 is then allowed to travel through a complete 10 mm cycle (i.e., 10 mm down and 10 mm back up). Consequently, the T-rod 1101 will make contact with the sample 1000 after about 5 mm and bend the sample about an additional 5 mm. The bending resistance is the peak force required to bend the sample as the T-rod travels through a complete 10 mm cycle.

Burst Strength Test

Overview

A test specimen, held between annular clamps, is subjected to increasing force that is applied by a 0.625 inch diameter, polished stainless steel ball. The burst strength is that force that causes the sample to fail. Burst strength may be measured on wet or dry samples.

| | |
|---|---|
| Apparatus | |
| Burst Tester | Intelect-II-STD Tensile Test Instrument, Cat. No. 1451-24PGB or the Thwing-Albert Burst Tester are both suitable. Both instruments are available from Thwing-Albert Instrument Co., Philadelphia, PA. The instruments must be equipped with a 2000 g load cell and, if wet burst measurements are to be made, the instruments must be equipped with a load cell shield and a front panel water shield. |
| Conditioned | Temperature and humidity should be controlled to remain |

| Apparatus | |
|---|---|
| Room | within the following limits:<br>Temperature:<br>73 ± 3° F.<br>(23° C. ± 2° C.)<br>Humidity: 50 ± 2% Relative Humidity |
| Paper Cutter | Scissors or other equivalent may be used |
| Pan | For soaking wet burst samples, suitable to sample size |
| Solution | Water for soaking wet burst samples should be equilibrated to the temperature of the conditioned room. |
| Timer | Appropriate for measuring soak time |

Sample Preparation

1) Cut the sample to a size appropriate for testing (minimum sample size 4.5 in×4.5 in.) If the sample to be tested is too small (e.g., a flexible extension with overall dimensions less than 4.5 in×4.5 in) a larger sample of the same material should be used to determine wet burst strength. Prepare a minimum of five samples for each condition to be tested.

2) If wet burst measurements are to be made, place an appropriate number of cut samples into a pan filled with temperature-equilibrated water.

Equipment Setup

1) Set the burst tester up according to the manufacturer's instructions. If an Intelect-II-STD Tensile Test Instrument is to be used the following are appropriate:

Speed: 12.7 centimeters per minute

Break Sensitivity: 20 grams

Peak Load: 2000 grams

2) Calibrate the load cell according to the expected burst strength.

Measurement and Reporting

1) Operate the burst tester according to the manufacturer's instructions to obtain a burst strength measurement for each sample.

2) Record the burst strength for each sample and calculate an average and a standard deviation for the burst strength for each condition.

3) Report the average and standard deviation for each condition to the nearest gram.

Report the average and the standard deviation for each group of four samples.

| Water Dispersion Test | |
|---|---|
| Apparatus | |
| Stirrer | Magnetic, Thermolyne type Model S7225 or 7200 (no substitutions). Permanently inscribe a circle 3.5 inches (8.9 centimeter) on the top surface of the stirrer. The center of the circle must be coincident with the geometric center of the stirrer. |
| Stirring Bar | 2.5 inch (6.2 centimeter) TEFLON coated with spinning ring. Permanently mark one end of the bar with black ink for a distance of 0.5 inch (1.2 centimeter) back from the tip. |
| Thermometer | 30 to 120° F. with 1 degree divisions |
| Timer | Digital stopwatch |
| Stroboscope | Variable speed stroboscope, model 964 available from Strobette, Power Instrument, Inc. of Skokie, IL is suitable |
| Beaker | Kimax brand 2000 milliliter with spout (no substitution), Inscribe a fill mark at a height of 5.6 inches (14.3 centimeters) from the flat bottom of the beaker. Do not use any beaker not having a flat bottom. |
| Conditioned Room | Temperature and humidity should be controlled to remain within the following limits:<br>Temperature: 73 ± 3° F. (23° C. ± 2° C.)<br>Humidity: 50 ± 2% Relative Humidity |

Test Setup

1. Fill the beaker to the fill mark with 73 ± 3° F. tap water.
2. Place the beaker on the magnetic stirrer centering it in the inscribed circle.
3. Add the stirring bar to the beaker.
4. Turn the stroboscope on and set the speed to 1000 rpm according to the manufacturer's directions.
5. Turn the magnetic stirrer on with the on/off switch. Adjust the speed of the magnetic stirrer until the stirring bar appears to be stationary and both ends appear to be black. This indicates that the magnetic stirrer is turning at 500 rpm (i.e. half the setting on the stroboscope). Turn the magnetic stirrer off with the on/off switch.

Procedure

1. Hold a sample (e.g. an absorbent interlabial device 20) 3 to 4 inches (7.6 to 10.2 centimeters) above the surface of the water. Gently drop the sample onto the water surface, starting the timer when the sample touches the water surface.
2. Wait 5 seconds.
3. Start the magnetic stirrer with the on/off switch. If the sample disrupts the rotation of the stirring bar, stop the stirrer, re-orient the bar, and immediately start the stirrer again.
4. Record the time required until the sample separates into at least two pieces. Separation does not include the disassociation of a few individual fibers from an otherwise intact sample. The time is the total time the sample is immersed in the water including the time the stirrer may have been stopped to re-orient the sample.
5. Repeat steps 1 through 4 with an additional 3 samples.

Calculation and Reporting

Calculate and report the mean and standard deviation of the water dispersibility time for the four samples tested.

Flushability Test

Overview

As noted above, the terms "flushable or flushability" refer to a product's capacity to pass through typical commercially available household toilets and plumbing drainage systems without causing clogging or similar problems that can be directly associated with the physical characteristics of the product. For the purpose of the appended claims, catamenial products are evaluated for flushability via relative ease of toilet bowl and trap evacuation and subsequent transport through a simulated plumbing system. The flushability of such a device should be measured by the following test procedure.

The test procedure is designed to simulate two days of normal toilet usage for a family of 4 (2 men, 2 women). The test employs a flushing sequence to simulate the following conditions: male urination visits, female urination visits (including post urinary drying with tissue), disposal of catamenial product (that is, the interlabial device or other device to be tested) with cleaning using tissue, and bowel movement visits. The amount of tissue to be used for each tissue flush is a normal loading of 2 strips of seven sheets. The normal loading is based on consumer research regarding typical habits and practices. The test is designed to simulate the conditions a product will encounter if it is flushed through a conventional toilet and into a municipal sewer or into a septic tank. Samples are evaluated for: 1) toilet bowl and trap clearance, 2) drain line blockage, and 3) disintegration during flushing.

Apparatus

Figure 12:
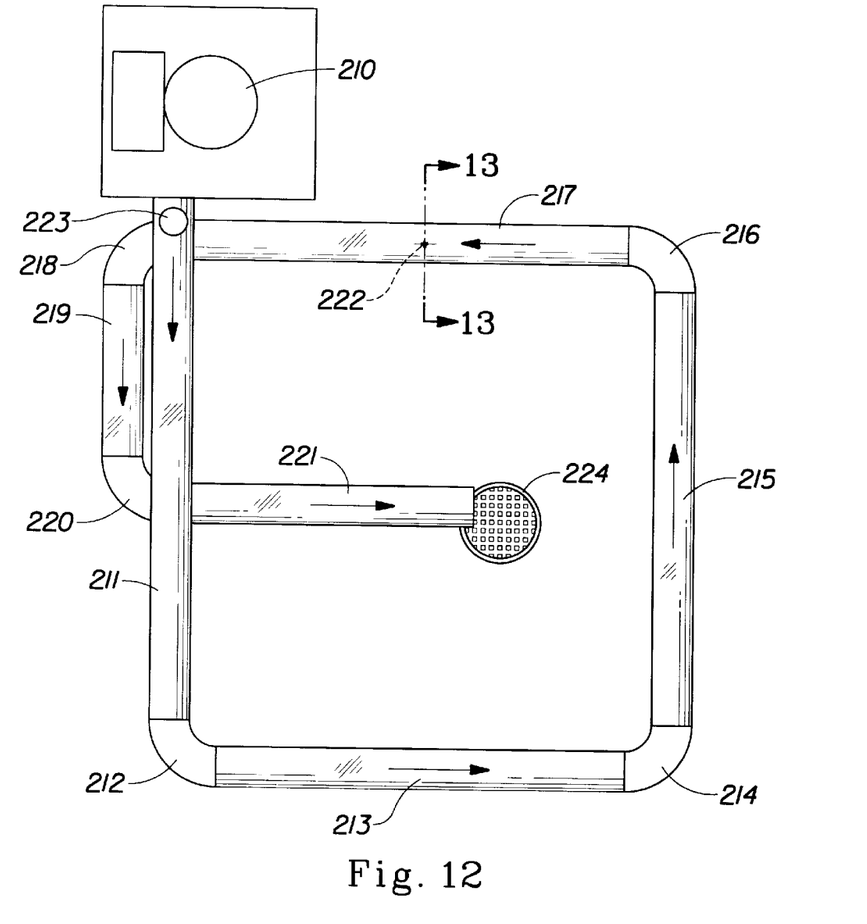
FIG. 12 is a plan view of an apparatus suitable for flushability determination according to the method described in the TEST METHODS section, below.
Figure 13:
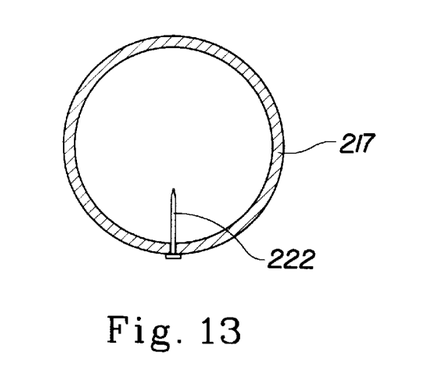
FIG. 13 is a cross-section of the flushability apparatus of FIG. 12 taken along line 13—13 thereof.

An apparatus suitable for the flushability test is shown in plan view in FIG. 12. The apparatus includes:

- a 3.5 gallon (13.2 liter) water saver siphon vortex toilet referred to as 210 (additional toilets can also be attached to the piping layout shown in FIG. 12 to evaluate the behavior of test samples using different flushing mechanisms such as commercial, pressure toilets);
- approximately 59 feet (18 meters) of 4 inch (10 cm) inside diameter acrylic pipe (As can be seen from FIG. 14, the piping is assembled in roughly a square configuration having linear runs 211, 213, 215, 217, 219, 221 approximately 10 feet (3 meters) long);
- a cast iron tee 223 slightly downstream of the toilet 210 that is open to the atmosphere for venting;
- five cast iron ninety degree elbows 212, 214, 216, 218, and 220;
- a snag 222 positioned vertically (FIG. 13) approximately 15 feet from the pipe's terminal end and approximately 1 inch (2.5 cm) long; and
- a screen (No. 4 Tyler sieve) to capture solid effluent for evaluation of disintegration.

The apparatus used for this method is set up to be equivalent to ANSI Standard A112.19.2M-1990 for Vitreous China fixtures. The piping is plumbed to provide a drop of 0.25 inch per foot (2 centimeters/meter) of pipe length.

Materials

Tissue Product used in Test: standard CHARMIN® toilet tissue manufactured by The Procter & Gamble Company of Cincinnati, Ohio.

Synthetic Fecal Material Prepared according to the method described below

Test Flushing Sequence

The test flushing sequence simulates 2 days of normal toilet usage for a family of 4 (2 men, 2 women; based on consumer habits and practices research). The sequence of 34 total flushes consists of 14 flushes with an empty bowl, 8 flushes with tissue only, 6 flushes with tissue and a catamenial product and 6 flushes with tissue and simulated fecal matter (SFM). When it is used, the SFM is placed in the bowl just prior to the addition of tissue. The SFM loading of 160 g±5 g consists of two 1 inch (2.5 centimeter)×4 inch (10 centimeter) pieces and one 1 inch (2.5 centimeter)×2 inch (5 centimeter) piece. Folded tissue strips (or the catamenial product) are placed in the bowl at 10 second intervals. Ten seconds after the final strip or catamenial product is placed into the bowl, the toilet is flushed. The flushing sequence is described below as a series of two routines combined in the following order:

Routine #1 (To be performed first 6 times for a total of 30 flushes)

1) Flush With Tissue Only—Take a drain line blockage reading 2 minutes after the water reaches the simulated obstruction, wait 1 additional minute, and move to step 2.
2) Flush With Empty Bowl. Take a drain line blockage reading 2 minutes after the water reaches the snag point and move to step 3.
3) Flush With Tissue and Catamenial Product—Take a drain line blockage reading 2 minutes after the water reaches the snag point, wait 1 additional minute, and move to step 4.
4) Flush With Empty Bowl. Take a drain line blockage reading 2 minutes after the water reaches the snag point and move to step 5.
5) Flush With Tissue and Simulated Fecal Matter (SFM). Take a drain line blockage reading 2 minutes after the water reaches the snag point, wait 1 additional minute.

Routine #2 (To be performed 1 time)

1) Flush With Tissue Only—Take a drain line blockage reading 2 minutes after the water reaches the snag point, wait 1 additional minute, and move to step 2.
2) Flush With Empty Bowl. Take a drain line blockage reading 2 minutes after the water reaches the snag point and move to step 3.
3) Flush With Tissue Only—Take a drain line blockage reading 2 minutes after the water reaches the snag point, wait 1 additional minute, and move to step 4.
4) Flush With Empty Bowl. Take a drain line blockage reading 2 minutes after the water reaches the snag point.

Total number of flushes per sequence is 34.

If, after the second flush in the flushing sequence, the product remains in the bowl or trap after flushing, the tissue and or catamenial product is plunged into the drainage line manually and the flushing sequence will continue. After completion of each trial loading, the drainage pipe will be cleared prior to beginning subsequent testing.

The above described flushing sequence is repeated three times for each test product.

Data Reporting

The degree of drain line blockage is determined by measuring the length of water dammed up behind the obstruction. Graduations are marked every 12 inches (30 centimeters) on the drainpipe upstream of the obstruction. Each one foot length that the water is backed up corresponds to 0.25 inch (0.6 centimeter) or 6.25% of blockage at the obstruction point. Test product residues which exit the drainpipe are also collected.

The following data are recorded for each evaluation:

1) Incidence of failure (%) of catamenial product to clear bowl and trap in one flush
2) Incidence of failure (%) of catamenial product to clear bowl and trap in two flushes
3) Incidence of product on simulated snag
4) Maximum level (%) of drain line blockage
5) Cumulative level (%) of drain line blockage over the 2 day simulated test period.

Preferably, the products described herein will completely clear the bowl at least about 70% of the time in two or fewer flushes, more preferably at least about 80% of the time in one flush, even more preferably at least about 90% of the time in one flush, and most preferably at least about 95% of the time in one flush. The products described herein will preferably have a maximum level of drain line blockage of less than or equal to about 80%. The products described herein will preferably have a cumulative level of drain line blockage over the 2 day simulated test period of less than or equal to about 50%.

Preparation of Synthetic Fecal Material

I. Materials Needed:

Feclone synthetic fecal matter (900 grams); (Available from Siliclone Studio, Valley Forge, Pa. as product BFPS-7 dry concentrate )

Tap water at 100° C. (6066 grams)

II. Equipment Needed:

Mixer (Available from Hobart Corp., Troy, Ohio as Model A200)

Extruder (Available from Hobart Corp., Troy, Ohio as Model 4812)

Disposable Centrifuge tubes with screw caps (50 ml) (Available from VWR Scientific, Chicago, Ill. as Catalog No. 21-008-176)

Water Bath to control temperature to 37° C.

III. Preparation:
1. Pour the 100° C. water into the mixing bowl of the mixer and add the dry Feclone concentrate.
2. Mix on low for 1 minute.
3. Mix on medium speed for 2 minutes.
4. After the material is well mixed, transfer to the extruder.
5. Using an ice pick, punch a small hole in the tip of each centrifuge tube.
6. Extrude the Feclone into the centrifuge tubes.
7. Cap the centrifuge tubes and store in the refrigerator.
8. Before using, put the tubes in the water bath at 38° C. This concludes the test.

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention.

What is claimed is:

1. An absorbent interlabial device insertable into the interlabial space of a female wearer said interlabial device comprising:

a central portion comprising an upper portion and a lower portion thereof, a pair of absorbent flexible extensions joined to said upper portion of said central portion and extending downwardly and outwardly therefrom, a liquid impervious backsheet joined to at least a part of said central absorbent portion and said pair of absorbent flexible extensions, wherein said pair of flexible extensions has a first absorbent capacity and said central portion has a second absorbent capacity, said first absorbent capacity being greater than said second absorbent capacity.

2. The absorbent device of claim 1 further comprising a rayon topsheet joined to at least a portion of said flexible extension.

* * * * *

UNITED STATES PATENT AND TRADEMARK OFFICE
CERTIFICATE OF CORRECTION

PATENT NO. : 6,171,292 B1
DATED : January 9, 2001
INVENTOR(S) : Garabedian et al.

Page 1 of 1

It is certified that error appears in the above-identified patent and that said Letters Patent is hereby corrected as shown below:

<u>Claim 1, column 7,</u>
Line 33, after the word member please delete "," insert -- s --.
Line 34, delete "mono filaments" and insert -- monofilaments --.

<u>Claim 6, column 7,</u>
Please delete the entire claim.

<u>Claim 18, column 8,</u>
Line 34, delete "catheters" and insert -- catheter, --.
Line 47, after the word comprising please insert -- a --.

Signed and Sealed this

Thirtieth Day of October, 2001

*Attest:*

NICHOLAS P. GODICI
*Attesting Officer*     *Acting Director of the United States Patent and Trademark Office*

UNITED STATES PATENT AND TRADEMARK OFFICE
CERTIFICATE OF CORRECTION

PATENT NO. : 6,171,292 B1  
DATED : January 9, 2001  
INVENTOR(S) : Thomas Ward Osborn Page 1 of 1

It is certified that error appears in the above-identified patent and that said Letters Patent is hereby corrected as shown below:

This certificate supersedes certificate of correction issued October 30, 2001, the number was erroneously mentioned and should be deleted since no certificate of correction was granted.

Signed and Sealed this

Twenty-fifth Day of December, 2001

Attest:

Attesting Officer

JAMES E. ROGAN  
*Director of the United States Patent and Trademark Office*